United States Patent [19]

Marzi et al.

[11] Patent Number: 5,053,424
[45] Date of Patent: Oct. 1, 1991

[54] 2-(N-ACYL)AMINO-6,7-DIMETHOXY TETRALINES, AND PHARMACEUTICAL COMPOSITIONS HAVING ANTIHYPERTENSIVE ACTIVITY CONTAINING SAME

[75] Inventors: Mauro Marzi; Maria O. Tinti; Licia Pacifici; Carla Franceschelli; Massimo Castorina, all of Rome, Italy

[73] Assignee: Sigma-Tau Industrie Farmaceutiche Riunite S.p.A., Rome, Italy

[21] Appl. No.: 559,052

[22] Filed: Jul. 30, 1990

[30] Foreign Application Priority Data

Jul. 31, 1989 [IT] Italy ................. 48254 A/89

[51] Int. Cl.$^5$ ................. C07D 209/20; C07D 233/39; A61K 31/405; A61K 31/16
[52] U.S. Cl. ................. 514/419; 548/496; 562/443; 562/448; 562/450; 514/563
[58] Field of Search ................. 548/496; 562/443, 448, 562/450; 514/419, 563

[56] References Cited

FOREIGN PATENT DOCUMENTS 1261855 9/1989 Canada ................. 548/496

Primary Examiner—David B. Springer
Attorney, Agent, or Firm—Oblon, Spivak, McClelland, Maier & Neustadt

[57] ABSTRACT 2-(N-acyl)amino-6,7-dimethoxy tetraline of general formula (I)

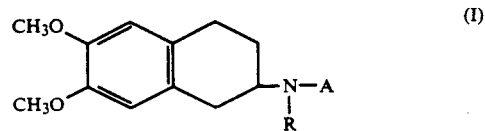

wherein R is selected from hydrogen and ethyl and A is an aminoacyl or dipeptidyl radical are endowed with potent anti-hypertensive activity.

13 Claims, No Drawings

2-(N-ACYL)AMINO-6,7-DIMETHOXY TETRALINES, AND PHARMACEUTICAL COMPOSITIONS HAVING ANTIHYPERTENSIVE ACTIVITY CONTAINING SAME

The present invention relates to 2-(N-acyl)amino-6,7-dimethoxy tetralines having general formula (I)

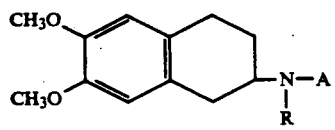

wherein R is selected from hydrogen and ethyl and A is an aminoacyl or dipeptidyl radical.

By "aminoacyl", the radicals glycyl, methionyl, tryptophyl and tyrosyl are preferably meant.

By "dipeptidyl", the radicals leucylalanyl, tryptophylalanyl, methionylalanyl and tyrosylalanyl are preferably meant.

The compounds of general formula (I) are endowed with potent antihypertensive activity.

The present invention also relates to the process for producing the compounds of general formula (I) and the pharmaceutical compositions which comprise a compound of general formula (I) as active ingredient.

Tetraline derivatives loosely related to the compounds of the present invention from a structural viewpoint are disclosed in UK patent 1,377,356 and in the European patent application 64964. However, in addition to being different in structure, the known tetraline derivatives possess pharmacological activities totally different from and unrelated to the antihypertensive activity shown by the compounds of general formula (I). In fact, the compounds of the British patent exhibit analgesic activity, while the compounds disclosed and claimed in the European patent application are active on the central nervous system and can be used for the therapeutical treatment of psychopathias such as schizophrenia.

The compounds of general formula (I) can be prepared via konwn processes. Synthesis of the compounds of general formula (I) wherein A is an aminoacyl radical (hereinbelow, compounds I') and of the compounds wherein A is a peptidyl radical (hereinbelow, compounds I") are briefly summarized hereinbelow in the following reaction schemes.

Synthesis scheme for the compounds of general formula (I) wherein A is the radical of an aminoacid.

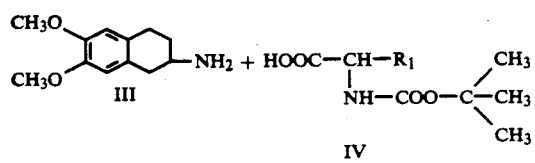

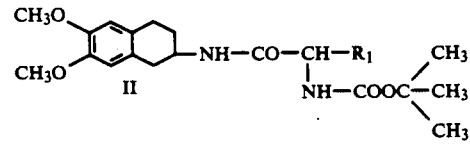

(a) HCOOH
(b) HCl

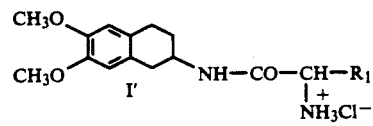

wherein the meaning of $R_1$ is described in table 1.

TABLE I

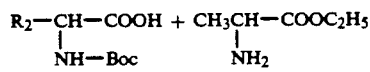

| $R_1$ | Reference name | A |
|---|---|---|
| H | ST 582 | glycyl |
| $-CH_2-CH_2-SCH_3$ | ST 581 | methionyl |
| 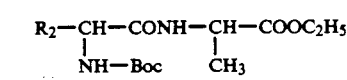 | ST 580 | tryptophyl |
| 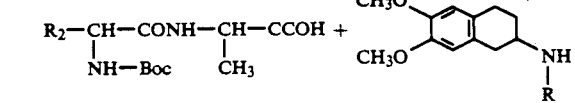 | ST 589 | tyrosyl |

Synthesis scheme of the compounds of general formula (I) wherein A is the radical of a dipeptide.

$$R_2-\underset{NH-Boc}{\underset{|}{CH}}-COOH + CH_3\underset{NH_2}{\underset{|}{CH}}-COOC_2H_5$$

$$\downarrow$$

$$R_2-\underset{NH-Boc}{\underset{|}{CH}}-CONH-\underset{CH_3}{\underset{|}{CH}}-COOC_2H_5$$

$$\downarrow OH^-$$

$$R_2-\underset{NH-Boc}{\underset{|}{CH}}-CONH-\underset{CH_3}{\underset{|}{CH}}-CCOH +$$

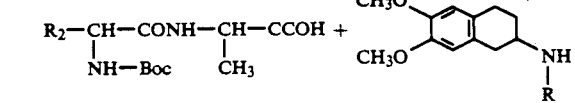

$$\downarrow$$

-continued

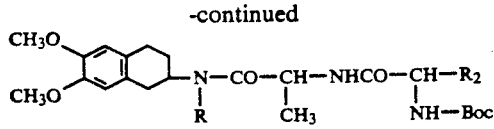

↓ H⁻

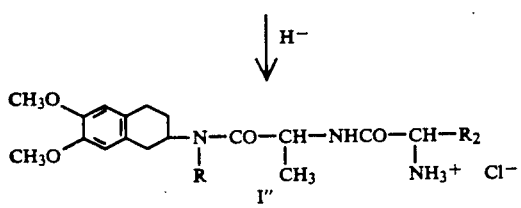

wherein the meaning of R and R₂ is described in table 2.

TABLE 2

| R₂ | R | Reference name | A |
|---|---|---|---|
| CH₃\CH—CH₂—/CH₃ | H | ST 584 | leucylalanyl |
| 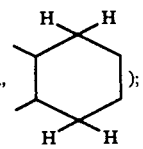 | H<br>CH₂CH₃ | ST 585<br>ST 604 | tryptophylalanyl<br>tryptophylalanyl |
| CH₃S—CH₂—CH₂— | H<br>CH₂CH₃ | ST 586<br>ST 606 | methionylalanyl<br>methionylalanyl |
| HO—⟨⟩—CH₂— | H | ST 605 | tyrosylalanyl |

EXAMPLE 1

Preparation of 2-N-glycylamino-6,7-dimethoxy tetraline hydrochloride (ST 582)

1st Step: Preparation of 2-(N-carbotertbutoxyglycyl)amino-6,7-dimethoxy tetraline 2-amino-6,7-dimethoxy tetraline (0.4 g; 2.07 mmoles) was dissolved in 20 ml CH₂Cl₂. Dicyclohexylcarbodiimide (0.4 g; 2.07 mmoles) and carbotertbutoxyglycine (0.36 g; 2.07 mmoles) were added to the solution. The solution was kept under stirring for 2 hours. Dicyclohexylurea that formed was then filtered off. The filtrate was extracted with a saturated solution of NaHCO₃, diluted HCl and H₂O till neutrality was reached. The organic phase separated and dried was concentrated under vacuum. The residue thus obtained was chromatographed on a silica gel column, eluting with CHCl₃—AcOEt, 1:1.

The collected fractions gave 0.6 g of the title compound; yield 86%; M.P. 124°–126° C. crystallized from cyclohexane.

NMR DMSO δ 7.9(1H, d, NH—CO); 6.9(1H, m, NH)6.7((2H, s,
         |
         Boc aromatic); 4.0(1H, m, ); 3.7(6H, s, 2-OCH₃); 3.5(2H, d, CH₂CO); 3.9–2.4(DMSO, m, ); 2.0–1.6(2H, m  H)1.5(9H, s, C(CH₃)₃)

2nd Step: Preparation of 2-N-glycylamino-6,7-dimethoxy tetraline hydrochloride The compound of the preceding step (0.33 g; 0.9 mmoles) was treated with 2 ml formic acid for 30 minutes at room temperature. The mixture was taken up with methylene chloride and extracted with H₂O and the acqueous phase was neutralized with NaHCO₃ and re-extracted with CH₂Cl₂. The separated and dried organic phase was concentrated under vacuum, thus furnishing 2-N-glycylamino-6,7-dimethoxy tetraline; M.P. 106°–108° C.; yield 62%.

The base thus obtained was dissolved in a saturated solution of HCl in ethanol. 2-N-glycylamino-6,7-dimethoxy tetraline hydrochloride was precipitated with ethyl ether and then crystallized with isopropanol; M.P. 225°–228° C.

NMR DMSO δ 8.7(1H, d, NHCO); 8.3(3H, m, NH₃); 6.7(2H, s, aromatic); 4.0(1H, m, ⟨—N); 3.7(6H, s, 2-OCH₃); 3.5(2H, m, CH₂CO); 2.9–2.5(4H, m, ⟨⟩); 2.1–1.5(2H, m,

EXAMPLES 2-4

Preparation of 2-N-methionylamino-6,7-dimethoxy tetraline hydrochloride (ST 581)

Preparation of 2-N-tryptophylamino-6,7-dimethoxy tetraline hydrochloride (ST 580)

Preparation of 2-N-tyrosyl-6,7-dimethoxy tetraline hydrochloride (ST 589)

ST 581, ST 580 and ST 589 were prepared as described in Example 1.

The reaction conditions and physico-chemical properties of the intermediates of general formula II and those of the compounds of general formula I' are illustrated in tables 3 and 4.

TABLE 3

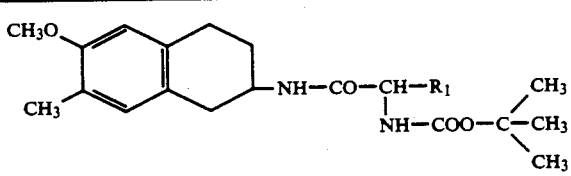

| $R_1$ | I step cs | reaction time | yield | M.P. °C. crystallization solvent | NMR DMSO δ |
|---|---|---|---|---|---|
| $CH_2CH_2SCH_3$ | 2 | 2 h | 78% | 119°-120° C. | 7.7(1H, d, NHCO); 6.8(1H, m, NH); 6.6(2H, d, aromatic); 4.1-3.6 (2H, m, H–C(CO)–H–NH ; CH); 3.7(6H, s, 2OCH$_3$); 2.9-2.2(6H, m ; CH$_2$S); 2.0(3H, s, SCH$_3$)1.9-1.6(4H, m, ; CH$_2$CH$_2$S)1.2(9H, s, C(CH$_3$)$_3$) |
| 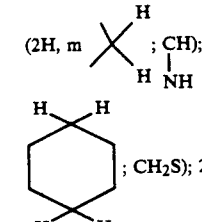 | 3 | 3 h | 73% | 188°-190° C. | 7.9-6.9(7H, m, aromatic tryptophane; NHCO; NHCOO); 6.5(2H, d, aromatic tetraline)4.3-3.8(2H, m, CH; NH N); 3.7(6H, s, 2OCH$_3$); 3.0(2H, m, —CH$_2$)2.7-2.4(4H, m ); 1.9-1.4(2H, m, H)1.2(9H, s, C(CH$_3$)$_3$) |
| 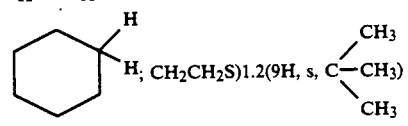 | 4 | 3 h | 90% | 126°-129° C. benzene | 9.1(H1, s, OH); 7.8(H1, d, aromatic tyrosine); 7.1(6H, d, aromatic tyrosine; NHCO NHCOO)6.5(2H, d, aromatic tetraline); 4.0(2H, m, CH; NH N ); 3.5(6H, s, 2OCH$_3$); 3.1-2.3(6H, m, —CH$_2$—; ); 2.1-1.6(2H, m, ); 1.4(9H, s, C(CH$_3$)$_3$) |

TABLE 4

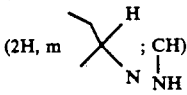

| R₁ | Es | reaction time | yield | M.P. °C. crystallization solvent | NMR DMSO δ |
|---|---|---|---|---|---|
| —CH₂CH₂SCH₃ | 2 ST 581 | 6.5 h | 75% | 96°–99° C. CH₃CN/ET₂O | (1H, d, NHCO); 8.3(3H, m, $\overset{+}{NH_3}$); 6.5(2H, s, aromatic); 3.9–3.7 (2H, m 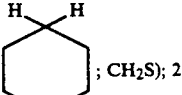; CH); 3.6(6H, s, 2OCH₃); 3.0–2.25(6H, m 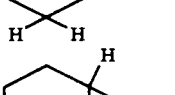; CH₂S); 2.0(3H, s, SCH₃)1.9–1.7(4H, m, 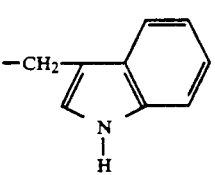); (CH₂CH₂S) |
| 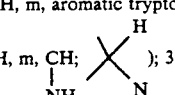 | 3 ST 580 | 3 h | 97% | 148°–149° C. | 8.7(4H, m, $\overset{+}{NH_3}$; CONH); 7.9–6.9(5H, m, aromatic tryptophane); 6.7(2H, d aromatic tetraline); 4.0(2H, m, CH; 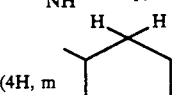); 3.7(6H, s, OCH₃); 3.3(2H, d, CH₂—); 2.9–2.3(4H, m 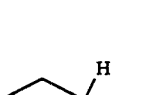); 1.8–1.3(2H, m 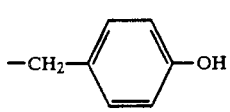) |
| 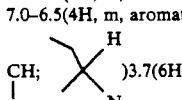 | 4 ST 589 | 3 h | 87% | dec. CH₃CN | 8.8–8.3(4H, m, NHCO; $\overset{+}{NH_3}$); 7.3–7.0(2H, d, aromatic tyrosine); 7.0–6.5(4H, m, aromatic tyrosine; aromatic tetraline); 4.0(2H, m, CH; 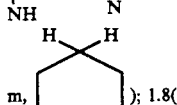)3.7(6H, s, 2OCH₃); 3.0(2H, d, CH₃); 2.9–2.4(4H, m, ); 1.8(2H, m 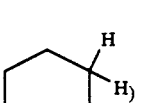) |

EXAMPLE 5

Preparation of 2-(N-leucylalanyl)amino-6,7-dimethoxy tetraline hydrochloride (ST 584)

1st Step: Preparation of N-carbotertbutoxy-leucylalanine ethyl ester

Triethylamine (1.4 ml; 0.001 moles) was added to carbotertbutoxy-L-leucine (2.5 g; 0.001 moles) dissolved in acetonitrile (50 ml).

Isobutyl chloroformate (1.3 ml; 0.001 moles) was added to the cooled solution under stirring at −15° C.

A solution of L-alanine ethyl ester hydrochloride (1.54 g; 0.001 moles) in 20 ml of acetonitrile and triethylamine (1.4 ml; 0.001 moles), prepared separately, was added to the mixture after 1 hour under stirring at −15° C.

The reaction mixture was kept under stirring at −15° C. for 2 hours and at room temperature for 4 hours, subsequently filtered and the filtrate concentrated under vacuum.

The residue thus obtained was taken up with ethyl acetate.

The precipitated triethylamine hydrochloride was filtered off and the ethyl acetate solution was extracted with diluted HCl, a saturated solution of NaHCO₃ and then with H2O till neutrality was reached.

The organic phase was separated and dried on anhydrous Na₂SO₄ and concentrated under vacuum. 2.35 g of a solid residue was thus obtained. M.P. 98°-100° C.

NMR CDCl₃ δ 7.2(1H, d, —NH—CO); 5.3(1H, d, NHBoc);

4.8(1H, t, C$\underline{H}$—   ); 4.5(3H, m, C$\underline{H}$—; OC$\underline{H}_2$—CH₃)
       |                              |
     NH—Boc                          CH₃

2.0-1.2(18H, m, CH—C$\underline{H}_2$; —C(CH₃)(CH₃)—C$\underline{H}_3$; C$\underline{H}_3$;
                                           |
                                          CH₃ CH CH₂C$\underline{H}_3$CH(CH₃)(CH₃)   ); 1.0(6H, d, CH(CH₃)(CH₃))

2nd Step: Preparation of N-carbotertbutoxy-leucylalanine 6 ml of 1N NaOH were added to a solution N-carbotertbutoxy-leucylalanine ethyl ester (1 g; 0.003 moles) dissolved in 7 ml of methanol.

The reaction mixture was kept at room temperature for 2 hours and then dried. The residue was dissolved in a mixture of H₂O and ethyl acetate.

The separated and dried organic phase was concentrated under vacuum. Yield 0.6 g; M.P. 73° C.

NMR CDCl₃ δ 7.5(1H, d, NHCO); 5.8(1H, d, NH—Boc)

4.9(1H, t, C$\underline{H}$  ); 4.5(1H, m, C$\underline{H}$); 2.0-1.3(15H, m, —CH—C$\underline{H}_2$,
       |                     |
     NH Boc                 CH₃

—C(CH₃)(CH₃)—C$\underline{H}_3$; CH₃C$\underline{H}$(CH₃)(CH₃)   ); 0.9(6H, d, CH(CH₃)(C$\underline{H}_3$))

TLC: silica gel; eluant ethyl acetate-methanol (80-20) R.F.=0.3

3rd Step: Preparation of 2-(N-carbotertbutoxy-leucylalanyl)amino-6,7-dimethoxy tetraline hydrochloride A solution of N-carbotertbutoxyleucylalanine (0.9 g; 0.003 moles) in 20 ml acetonitrile was added to a solution of 2-amino-6,7-dimethoxy tetraline (0.7 g; 0.003 moles) in 20 ml acetonitrile.

Dicyclohexylcarbodiimide (0.6 g; 0.003 moles) in 10 ml acetonitrile was added to the solution thus obtained.

The reaction mixture was kept under stirring at room temperature for 4 hours, then filtered and the filtrate was concentrated under vacuum. The residue thus obtained was dissolved with ethyl acetate.

The solution was extracted with a saturated solution of NaHCO₃, H₂O, diluted HCl and H₂O.

The separated and dried organic phase was concentrated under vacuum. An oily residue was thus obtained, yield 0.4 g.

NMR CDCl₃ 7.5(2H, m, 2NH—CO); 7.0(2H, m, [phenyl ring]);

5.5(1H, m, NH—Boc); 4.8-4.2(3H, m, C$\underline{H}$; C$\underline{H}$; )4.0(6H,
                                     |   |
                                    NH  CH₃ s, 2OCH₃); 3.2-2.8(4H, m, [cyclohexane ring] )2.2-1.3(17H, m,

[cyclohexyl], C$\underline{H}$(CH₃)(CH₃), —CH₂—, C$\underline{H}_3$, C(CH₃)(CH₃)—CH₃;
                                              |
                                             CH 1.0(6H, d, —CH(C$\underline{H}_3$)(C$\underline{H}_3$) )

TLC: silica gel; eluant ethyl acetate-methanol (80-20) R.F=0.8

4th Step: Preparation of 2-(N-leucylalanyl)amino-6,7-dimethoxy tetraline hydrochloride (ST 584)

2-(N-carbotertbutoxy-leucylalanyl)amino-6,7-dimethoxy tetraline (6.5 g; 0.01 moles) was dissolved in 36 cc trifluoroacetic acid and the solution was kept under stirring at room temperature for 30 minutes. To the solution ethyl ether was added, the solid thus obtained was separated by decantation and washed several times with ethyl ether. The residue dissolved in methanol was eluted on strong basic resin Amberlist A26 column activated in OH⁻ form. To the eluted methanol solution HCl in isopropanol was added until pH 3 was reached, the hydrochloride product was precipitated with ethyl ether. The solid thus obtained was separated by filtration furnishing 1,5 g. M.P. 85°-86° C.

TLC: silica gel; eluant ethyl acetate-methanol (80-20) R.F.=0.3

NMR CDCl₃ δ 7.8(1H, d, NHCO); 6.8(1H, d, NHCO); 6.5(2H, m,

[phenyl ring] ); 4.5-4.0(3H, m, —C$\underline{H}$ ; C$\underline{H}$ N); 3.8(6H, s,
                                  |     |
                                 CH₃   NH₂

2OCH₃); 3.0-2.5(4H, m, [cyclohexane ring] ); 2.0-1.3(8H, m,

-continued

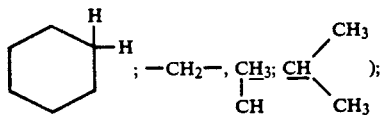

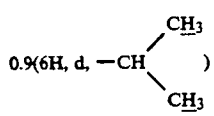

EXAMPLE 6

Preparation of 2-(N-triptophylalanyl)amino-6,7-dimethoxy tetraline hydrochloride (ST 585)

1st Step: Preparation of N-carbotertbutoxy-triptophylalanyl ethyl ester

L-alanine ethyl ester hydrochloride (2.5 g; 0.016 moles) was dissolved in 100 ml acetonitrile.

Triethylamine (2.3 g; 0.016 moles), carbotertbutoxy L-triptophane (5.0 g; 0.016 moles) and dicyclohexylcarbodiimide (3.4 g; 0.016 moles) were added to the solution.

The mixture was kept at room temperature overnight under magnetic stirring. The solution was then filtered to remove dicycloesylurea that formed and concentrated under vacuum. The residue was taken up with ethyl acetate, the solution was filtered and subsequently extracted with a saturated solution of $NaHCO_3$, diluted HCl and then with $H_2O$. The organic phase, separated and dried on anhydrous $Na_2SO_4$, was concentrated to dryness. 6 g of the product were obtained.

TLC: silica gel; eluant: ethyl acetate-methanol (60–40) R.F.=0.8

NMR $CDCl_3$ δ 8.4(1H, m, CONH); 7.7–7.0(5H, m, aromatic);

6.5(1H, d, NH—COO); 5.2(1H, m, —CH—; CH_3); 4.5(1H, m, —CH—; NH);

4.0(2H, q, —CH_2—CH_3); 1.8–1.00(15H, m, —C(CH_3)_3; CH_3);

CH_3; —CH_2CH_3)
|
CH

2nd Step: Preparation of N-carbotertbutoxytryptophylalanine

The product was obtained as described in step 2 of Example 5.
M.P.. 112° C.
TLC: silica gel; eluant ethyl acetate-methanol (60–40) R.F.=0.5

3rd Step: Preparation of 2-(N-carbotertbutoxy-tryptophylalanyl)amino-6,7-dimethoxy tetraline The product was obtained as described in step 3 of Example 5.

TLC: silica gel; eluant ethyl acetate-hexane (80–20)
R.F. 0.4

NMR $CDCl_3$ 8.6(1H, m, NHCO); 7.7–7.0(6H, m, aromatic tryptophane); 6.8–6.3(3H, m, NHCO, aromatic tetraline); 5.2(1H, d, —NH—); 4.5–4.0(2H, m, CH—; CH); 3.8(6H, s, 2OCH_3);
|       |       |
Boc    CH_3    NH

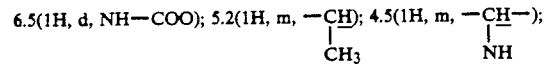

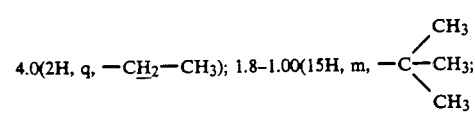

4th Step: Preparation of 2-(N-tryptophylalanyl)amino-6,7-dimethoxy tetraline hydrochloride (ST 585)

The product was prepared as described in step 4 of Example 5.

TLC: silica gel; eluant ethyl acetate-methanol (80–20)
R.F. 0.3
E.A. $C_{26}H_{33}ClNO_4$, 3.2% $H_2O$ NMR $CDl_3$ 8.6(1H, m, NHCO); 7.9–7.0(6H, m, aromatic tryptophane); 7.8–6.3(3H, m, NH—CO; aromatic tetraline)

4.6–4.0(2H, m, CH; CH); 3.5(2H, d, CH—CH_2); 3.0–2.6(4H, m, CH_3NH

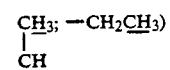

The compounds:
2-(N-methionylalanyl)amino-6,7-dimethoxy tetraline hydrochloride (ST 586);
2-(N-ethyl,N-methionylalanyl)amino-6,7-dimethoxy tetraline hydrochloride (ST 606);
2-(N-ethyl,N-tryptophylalanyl)amino-6,7-dimethoxy tetraline hydrochloride (ST 604);
2-(N-tyrosylalanyl)amino-6,7-dimethoxy tetraline hydrochloride (ST 605)
were prepared as described in Example 6.

In particular the products ST 604 and ST 606 were obtained (4th step) by condensing the suitable N-Boc dipeptite with 2-(N-ethyl)amine-6,7-dimethoxy tetraline prepared as described in Example 6 of the Italian patent application 48779 A/86.

The working conditions and physico-chemical data of the compounds are described in table 5.

TABLE 5

| E. | yield | M.P. °C. | E.A. | NMR δ |
|---|---|---|---|---|
| E.7 ST 586 | 74% | hygroscopic | calc.<br>C % 58.65; H % 7.63<br>N % 10.26; S % 7.83<br>found<br>C % 58.86; H % 7.68<br>N % 10.03; S % 7.65 | 7.0(1H, d, NHCO); 6.8–6.4(3H, m-NH—CO—; aromatic tetraline); 4.5–4.0 (2H, m, C$\underline{H}$—C$\underline{H}$); 3.8(6H, s, 2CH$_3$O—); 3.0–2.3(6H, m, —CH$_3$—S; CH$_3$ NH$_3^+$) 2.1(3H, s, S—CH$_3$); 1.9(5H, m, ; CH$_2$CH$_2$S); 1.3(3H, d CH$_3$) CH |
| E.8 ST 604 | 58% | 170° C. | calc.<br>C % 64.25; H % 7.06;<br>N % 10.33; Cl % 6.54<br>found<br>C % 61.44; H % 7.35;<br>N % 9.78; Cl % 6.42<br>H$_2$O 4.6% | DMSO<br>8.8(1H, m, NHCO); 8.2(1H, m, —NH—CO)7.6–7.0(5H, m, aromatic tryptophane 6.7(2H, m, aromatic tetraline); 5.0–4.3(2H, m, C$\underline{H}$; C$\underline{H}$); 3.7 CH$_3$ NH$_3^+$ (6H, s, 2CH$_3$O); 3.5–3.0(6H, m, N ; CH$_2$ ) 2.8(2H, m, C$\underline{H}_2$CH) 2.1–1.7(2H, m, )1.2(6H, m, C$\underline{H}_3$; CH$_2$CH$_2$) CH |
| E.9 ST 606 | 89% | 118°–120° C. | calc<br>C % 55.74; H % 7.65;<br>H % 8.86; Cl % 7.48;<br>S % 6.76<br>found<br>C % 53.80; H % 7.42;<br>N % 8.90; Cl % 7.45;<br>S % 6.61 H$_2$O 3.6% | DMSO<br>8.9(1H, d, NHCO); 8.4(1H, m; NHCO); 6.7(2H, m, aromatic tetraline); 5.0–4.5(2H, m, C$\underline{H}$; C$\underline{H}$); 3.9(6H, s, 2CH$_2$O); 3.4(4H, m, CH$_2$S; N—CH$_2$) CH$_3$ NH$_3$ 3.0–2.5(4H, m, ); 2.2–1.8(7H, m, ; CH$_3$—S; CH$_2$CH$_2$); 1.5–1.0(6H, m, CH$_2$CH$_3$C$\underline{H}_3$) CH |
| E.10 ST 605 | 50% | 155°–158° C. | calc.<br>C % 60.30; H % 6.74<br>N % 8.70<br>found<br>C % 56.14; H % 6.53<br>N % 7.90<br>H$_2$O 2.85% | 8.0(1H, d, NHCO); 7.2–6.7(4H, m, tyrosine)6.4(3H, d, NHCO; aromatic tetraline)4.5–4.0(C$\underline{H}$; C$\underline{H}$); 3.8(6H, s, 2CH$_3$O)2.8(4H, m, ); 1.9 NH CH$_3$ (2H, m ) 1.3(3H, d, C$\underline{H}_3$) CH |

The low toxicity and the potent antihypertensive activity of the compounds of the present invention were assessed via several tests. The methods employed and the results of some of these tests are illustrated hereinbelow.

Toxicological Tests (a) Tolerability

Male albino Swiss mice weighing 22–24 g were used in this test.

One group of animals (4/dose) which had been kept fasting for 18 hours was orally administered the compounds dissolved in twice distilled water. The same compounds dissolved in saline at pH=7 were intravenously injected in a further group of animals which had free access to food and drinking water. All of the animals were monitored for 7 days.

The test results are reported in the first column of table 7.

(b) LD50

LD50 was assessed according to the Carrol S. WEIL's method (Biometrics, pages 249-163 (1952)) on male Albino Swiss mice weighing 22–24 g. The compounds dissolved in 9% saline solution were administered via the intravenous route. The results are illustrated in table 6.

TABLE 6

| Compound | LD50 mg/kg | from mg/kg | to mg/kg |
| --- | --- | --- | --- |
| ST 580 | 66.67 | 60.44 | 73.53 |
| ST 581 | 74.03 | 65.58 | 83.57 |
| ST 582 | 72.29 | 72.29 | 72.29 |
| ST 584 | 167.04 | 153.96 | 181.23 |
| ST 585 | 115.20 | 106.18 | 124.98 |
| ST 586 | 228.87 | 240.18 | 347.43 |
| ST 589 | 217.84 | 195.40 | 242.86 |
| ST 604 | 85.01 | 77.08 | 93.76 |
| ST 605 | 72.29 | 72.29 | 72.29 |
| ST 606 | 150.41 | 136.37 | 165.90 |

Pharmacological Tests (a) Measure of arterial pressure in cats.

Normotensive cats of either sex weighing 2.5–3.5 kgs were used in this test.

The animals fasted for 18 hours were anesthetized with Na Nembutal (30 mg/kg) and ethyl urethane (300 mg/kg i.p.). The crural vein and artery of the animals were cannulated, the former for administering the compounds, the latter for monitoring the arterial pressure. The arterial pressure was measured via a mercury gauge connected to a rotating kymograph.

The compounds were dissolved in sterile 0.9% saline and administered at physiological pH in a 0.5 ml/kg volume.

The results are illustrated in the second column of table 7.

(b) Non-invasive measure of arterial pressure in genetically hypertensive rats.

Male SHR rats (Charles River) of 3–4 months were used in this test. The compounds listed were dissolved in either 0.9% saline or twice distilled water and administered via the oral route or i.p. (50–100 mg/5 ml/kg).

The animals, housed in individual cages at 23° C. and 60% humidity, had free access to food and drinking water. A BP recorder (Letica) equipped with a two-way polygraph was used. The systolic and diastolic pressure and the heart rate were recorded. The animals, a few days before the test began, were accustomed to be constrained on a heating plate (at 38° C.±1° C.) for 20 minutes).

During the pre-tests, the assessments were made at time 0 ($8^{30}$–$9^{30}$ a.m.) and after 1, 2 and 4 hours.

Every assessment was the average of 3 measures and the maximum residence time of the animal in the thermostatized chamber (for the whole test duration) was 40 minutes.

Student's "t" test was used for assessing the difference with respect to the control group and its own 0 time.

The results are shown in the third column of table 7.

TABLE 7

| | I TOLERABILITY dose mg/kg | | II HYPOTENSIVE EFFECT IN NORMOTENSIVE CATS dose mg/kg | | III ANTIHYPERTENSIVE EFFECT IN SHR HYPERTENSIVE RATS | | | |
| --- | --- | --- | --- | --- | --- | --- | --- | --- |
| | | | | hypotension | | mm Hg | | |
| COMPOUNDS | os | e.p. | mm Hg | | doses mg/kg | $1^{st}$ h | $2^{nd}$ h | $4^{th}$ h |
| ST 580 | >50 | >50 | 1–4 mg | 0 | — | — | — | — |
| ST 581 | " | " | 1–4 mg | 0 | — | — | — | — |
| ST 582 | " | " | 10 mg | −12S | 50 i.p. | −37 | −27 | 0 |
| | | | 20 mg | −66L | | | | |
| ST 584 | " | " | 4 mg | −20A | 10C os | −12 | 0 | 0 |
| ST 585 | " | " | 4 mg | 0 | — | — | — | — |
| | | | 10 mg | −46S | | | | |
| ST 586 | " | " | 2 mg | 0 | — | — | — | — |
| | | | 4 mg | −14S | | | | |
| ST 589 | " | " | 1 mg | −10S | 100 os | −26 | −20 | 0 |
| | | | 2 mg | −14S | | | | |
| | | | 4 mg | −60L | | | | |
| ST 604 | " | " | 1–4 mg | 0 | — | — | — | — |
| ST 605 | " | " | 1 mg | 0 | 100 e.p. | −40 | −38 | −29 |
| | | | 2 mg | −10S | 100 os | | −28* | −31* |
| | | | 4 mg | −14A | — | | −35** | −17** |
| ST 606 | " | " | 1 mg | −10S | — | — | — | — |
| | | | 2 mg | −12S | | | | |
| | | | 4 mg | −18S | | | | |

EFFECT DURATION:
S = short
A = average
L = long
ADMINISTRATION ROUTES:
os = oral
i.p. = intraperitoneal
i.v. = intravenous
*single administration
**repeated administration (5 days).

The dose of the compounds of formula (I) to be administered will be determined having regard to the age, weight and general conditions of the patient. Effective results can be obtained with doses of about 0.5–5 mg/kg body wight/day. Because of the low toxicity of the compounds of the present invention larger doses can be administered, such as 8–10 mg/kg body weight/day.

The compounds of the present invention can be formulated by procedures well-known to those skilled in the pharmaceutical technology into the usual administration forms which comprise orally or parenterally administrable solid and liquid unit dosage forms. These unit dosage forms comprise from about 20 to about 50 mg of the active principle, in addition to the usual excipients.

What is claimed is:

1. A compound of formula (I)

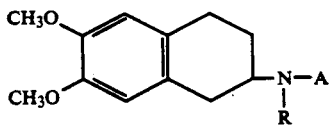
(I)

wherein R is selected from hydrogen and ethyl and A is an aminoacyl radical selected from glycyl, methionyl, tryptophyl and tyrosyl, or a dipeptidyl radical selected from leucylalanyl, tryptophylalanyl, methionylalanyl and tyrosylalanyl.

2. As a compound of claim 1, 2-N-glycylamino-6,7-dimethoxy tetraline hydrochloride.

3. As a compound of claim 1, 2-N-methionyl-amino-6,7-dimethoxy tetraline hydrochloride.

4. As a compound of claim 1, 2-N-tryptophyl-amino-6,7-dimethoxy tetraline hydrochloride.

5. As a compound of claim 1, 2-N-tyrosyl-amino-6,7-dimethoxy tetraline hydrochloride.

6. As a compound of claim 1, 2-(N-leucylalanyl)amino-6,7-dimethoxy tetraline hydrochloride.

7. As a compound of claim 1, 2-(N-tryptophylalanyl)amino-6,7-dimethoxy tetraline hydrochloride.

8. As a compound of claim 1, 2-(N-methionylalanyl)amino-6,7-dimethoxy hydrochloride.

9. As a compound of claim 1, 2-(N-ethyl,N-methionylalanyl)amino-6,7-dimethoxy tetraline hydrochloride.

10. As a compound of claim 1, 2-(N-ethyl, N-tryptophylalanyl)amino-6,7-dimethoxy tetraline hydrochloride.

11. As a compound of claim 1, 2-(N-tyrosylalanyl)amino-6,7-dimethoxy tetraline hydrochloride.

12. An orally or parenterally administrable pharmaceutical composition comprising an amount of one of the compounds of formula I of claim 1 effective to bring about a pressure decrease in a hypertensive subject, and a pharmacologically acceptable excipient.

13. The pharmaceutical composition of claim 12, in unit dosage form, comprising from about 20 to about 50 mg of one of the compounds of formula I.

* * * * *